United States Patent [19]

Gilad et al.

[11] 4,433,051

[45] Feb. 21, 1984

[54] DERIVATIVES OF α-DIFLUOROMETHYLORNITHINE USEFUL IN ANALYSIS

[75] Inventors: Gad Gilad; Varda Gilad, both of Ness Ziona; Meir Wilchek, Rehovot, all of Israel

[73] Assignee: Yeda Research and Development Co., Ltd., Rehovot, Iceland

[21] Appl. No.: 311,981

[22] Filed: Oct. 14, 1981

[51] Int. Cl.³ .................. G01N 33/50; C12Q 1/00; C12N 9/99; C12N 9/88

[52] U.S. Cl. .................................. 435/7; 435/4; 435/184; 435/232; 548/303; 549/349; 424/3; 436/546; 436/543

[58] Field of Search .............. 424/3, 7.1; 435/4, 7, 435/188, 810, 184, 232; 436/514, 515, 516, 543, 546, 800; 549/349; 548/303

[56] References Cited

U.S. PATENT DOCUMENTS

| | | | |
|---|---|---|---|
| 2,937,186 | 5/1960 | Burckhalter et al. | 436/546 |
| 4,134,792 | 1/1979 | Boguslavski et al. | 435/4 |

OTHER PUBLICATIONS

Metcalf et al., "Catalytic Irreversible Inhibition of Mammalian Ornithine Decarboxylase by Substrate and Product Analogues", *J.A.C.S.*, vol. 100, No. 8 (1978), pp. 2551–2553.

Gennis et al., "Singlet Energy-Transfer Studies on Associating Protein Systems, Distance Measurements on Trypsin, α-Chynotrypsin and Their Protein Inhibitors", *Biochemistry*, vol. 11, No. 13 (1972), pp. 2517–2524.

Gilad, Gad M. et al., "Histochemical Localization of Ornithine Decarboxylase with a Labelled Suicidal Enzyme Inhibitor", *Biochemical and Biophysical Research Communications*, vol. 96, No. 3, 1980, pp. 1312–1316.

*Primary Examiner*—Esther M. Kepplinger
*Attorney, Agent, or Firm*—Browdy and Neimark

[57] ABSTRACT

There are provided novel labelled derivatives, namely α-difluoromethylornithine tagged with rhodamine or with biotin. These are of value in analysis and in the cytochemical localization of enzymes.

4 Claims, No Drawings

DERIVATIVES OF α-DIFLUOROMETHYLORNITHINE USEFUL IN ANALYSIS

SUMMARY OF THE INVENTION

The present invention relates to novel derivatives of α-difluoromethylornithine (α-dFMO) which are useful in cytochemical analysis. α-dFMO is an enzyme activated irreversible inhibitor of ornithine decarboxylase (ODC) and its localization is of importance in various tests and especially in cytochemical localizations of enzymes. According to the present invention α-dFMO is coupled to specific molecules, and thus it is rendered visible. Amongst the molecules to which it may be coupled without loss of its enzymatic inhibitory activity there may be mentioned rhodamine, in which case the rhodamine-labelled inhibitor may be used for direct visualization in fluorescence microscopy or by similar techniques; or it may be coupled to biotin, and the biotin-labelled inhibitor can be used for indirect detection of the enzyme following its binding to avidin conjugated to a suitable peroxidase, such as horseradish peroxidase and visualization of the peroxidase reaction product.

The α-difluoromethylornithine can be labelled with the different marker molecules, while maintaining its activity as an inhibitor.

DESCRIPTION OF THE PREFERRED EMBODIMENT

The following examples illustrate the tagging of α-dFMO, with rhodamine-B-isothiocyanate and with biotin, respectively.

EXAMPLE 1: Preparation of α-dFMO tagged with rhodamine-B-isocyanate

Rhodamine-labelled inhibitor: The inhibitor was dissolved in H₂O and reacted with excess cupric carbonate to mask the α-amino group from reacting with the rhodamine label, leaving the α-amino group free. Rhodamine-B-isothiocyanate (Sigma) was mixed, using a 100:1 (inhibitor:rhodamine) molar ratio, with the inhibitor-copper chelate in a 0.4 M sodium carbonate-bicarbonate buffer, pH 8.4, overnight at 4° C. The mixture was then brought to pH 3 with HCl and the precipitate formed, washed and lyophilized. The preparation was dissolved in Tris-HCl buffer, pH 7.2, filtered, passed through a column of Sepharose coupled to lysine and the eluate, cleared from excess free rhodamine, used for biochemical and cytochemical studies.

The obtained rhodamine-labelled α-dFMO has the formula:

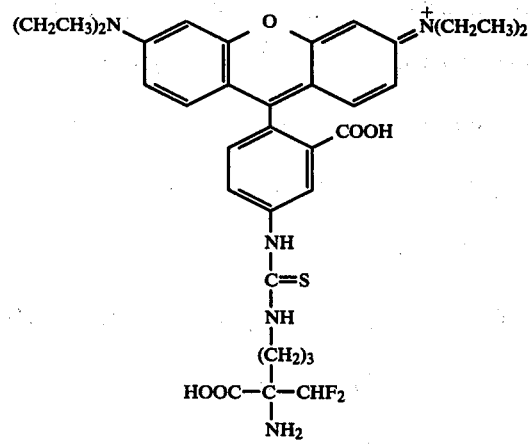

EXAMPLE 2: Preparation of α-dFMO tagged with biotin

Biotinyl-N-hydroxysuccinimide synthesized according to Bayer and Wilchek, (Meth. Enzymol. 46, 613, (1977)) was dissolved in dimethyl-formamide and added slowly in a 1:1 ratio to an inhibitor-copper chelate in a carbonate-bicarbonate buffer, pH 8.6, and mixed for 2 hours at room temperature. The supernatant was decanted, H₂S was added and the precipitate formed was lyophilized and then redissolved in Tris-HCl buffer, pH 7.2, and used for cytochemical studies. The obtained biotin-labelled α-dFMO has the formula:

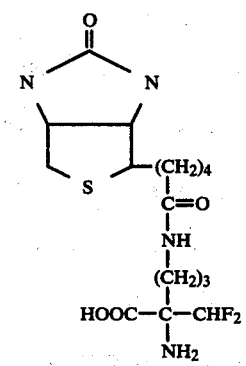

EXAMPLE 3

The final reaction products from both Example 1 and Example 2 were separated by high voltage paper electrophoresis according to Degani and Patchornik (Biochem, 13 (1):1, (1974)), and identified by characteristic color reactions. The inhibitor α-dFMO identified by the ninhydrin reaction, was not present either in the rhodamine-labelled inhibitor preparation (IR, identified by the rhodamine color and fluorescence) or in the biotin-labelled preparation (IB, identified by a specific color reaction for biotin). The labelled reagents could be extracted with water.

EXAMPLE 4: Retention of inhibitory activity by labelled α-dFMO

Following the synthesis of the conjugated inhibitor and its isolation according to the methods outlined, the inhibition of ODC activity by the product was examined in tissue homogenates. Rhodamine-labelled α-dFMO inhibited 43% and biotin-labelled 64% of the enzyme activity present in 7 day old rat cerebellum. Rhodamine or biotin alone were completely devoided of inhibitory activity.

RETENTION OF ODC ACTIVITY FOLLOWING TISSUE FIXATION

Fixation reduced ODC activity to a certain extent. However, in spite of this reduction, substantial enzyme activity still remained in the tissues examined.

The present invention shows that the specific enzyme activated irreversible inhibitor of the enzyme ODC-α-dFMO-, can be labelled, and still retain its inhibitory activity, with specific molecules (tags) which render it visible by light and fluorescence microscopy. Rhodamine-B-isothiocyanate served as the fluorescent tag and made it possible to directly visualize the tissue localization of the labelled inhibitor by fluorescence microscopy. Biotin-labelled inhibitor was visualized indirectly via the brown reaction product catalyzed by HRP-conjugated avidin which binds specifically and strongly to biotin. Using this procedure ODC has been localized in tissue sections of rat brain and liver.

We claim:

1. A labelled derivative of α-difluoromethylornithine (α-dFMO), namely α-dFMO tagged with rhodamine B or with biotin, respectively, of the formulas

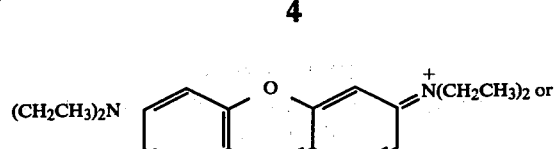

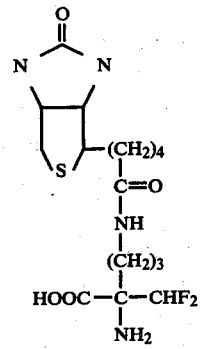

2. A process for tagging α-dFMO with rhodamine B which comprises dissolving the inhibitor in water, reacting same with an excess of cupric carbonate, adding rhodamine-B-isothiocyanate to the inhibitor-copper chelate at a pH of about 8.4, acidifying to pH 3, washing and lyophilizing the precipitate, dissolving same in Tris-HCl buffer, pH 7.2.

3. A process for preparing α-dFMO coupled to biotin which comprises preparing an enzyme-copper chelate as defined in claim 2, dissolving biotinyl-N-hydroxysuccinimide in a suitable solvent and admixing these two components in a carbonate/bicarbonate buffer pH 8.6, decanting after an adequate period of reaction, adding hydrogen sulfide and lyophilizing the precipitate.

4. A process for the cytochemical localization of ornithine decarboxylase (ODC) activity comprising:
  subjecting tissue samples to the action of an enzyme activated irreversible inhibitor of ODC which inhibitor has been labelled with specific molecules which render it visible by light or fluorescence microscopy; and
  visually localizing the labelled inhibitor by light or fluorescence microscopy,
  wherein said enzyme activated irreversible inhibitor of ODC is an α-dFMO derivative in accordance with claim 1.

* * * * *